(12) United States Patent
Gerberding et al.

(10) Patent No.: US 6,315,790 B1
(45) Date of Patent: Nov. 13, 2001

(54) RADIOPAQUE MARKER BANDS

(75) Inventors: Brent C. Gerberding, Minneapolis; Brooke Qin Ren, Champlin, both of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/327,234

(22) Filed: Jun. 7, 1999

(51) Int. Cl.[7] ................................................. A61F 11/00
(52) U.S. Cl. ............................................................ 623/1.11
(58) Field of Search .................................. 606/108, 195, 606/198, 194; 623/1.11, 1.23

(56) References Cited

U.S. PATENT DOCUMENTS

| | | |
|---|---|---|
| 4,740,207 | 4/1988 | Kreamer . |
| 4,866,132 | 9/1989 | Obligin et al. . |
| 4,893,623 | 1/1990 | Rosenbluth . |
| 4,950,227 | 8/1990 | Savin et al. . |
| 5,007,926 | 4/1991 | Derbyshire . |
| 5,024,232 | 6/1991 | Smid et al. . |
| 5,045,080 | 9/1991 | Dyer et al. . |
| 5,256,334 | 10/1993 | Smid et al. . |
| 5,429,597 | 7/1995 | DeMello et al. . |
| 5,480,423 | 1/1996 | Ravenscroft et al. . |
| 5,609,625 | 3/1997 | Piplani et al. . |
| 5,632,760 | 5/1997 | Sheiban et al. . |
| 5,643,278 | 7/1997 | Wijay . |
| 5,653,691 | 8/1997 | Rupp et al. . |
| 5,733,299 | 3/1998 | Sheiban et al. . |
| 5,759,174 | 6/1998 | Fischell et al. . |
| 5,792,144 * | 8/1998 | Fischell et al. ..................... 606/108 |
| 5,824,058 | 10/1998 | Ravenscroft et al. . |
| 5,843,090 | 12/1998 | Schuetz . |
| 5,876,445 | 3/1999 | Andersen et al. . |
| 5,910,145 | 6/1999 | Fischell et al. . |
| 5,948,489 | 9/1999 | Hopkins . |
| 5,951,569 | 9/1999 | Tuckey et al. . |
| 5,968,052 | 10/1999 | Sullivan, III et al. . |
| 5,989,280 * | 11/1999 | Euteneuer et al. ................. 606/198 |
| 6,019,778 | 2/2000 | Wilson et al. . |
| 6,024,740 * | 2/2000 | Lesh et al. ............................ 606/34 |
| 6,027,510 * | 2/2000 | Alt ...................................... 606/108 |
| 6,056,759 * | 5/2000 | Fiedler ................................. 606/108 |

* cited by examiner

Primary Examiner—Jeffrey A. Smith
Assistant Examiner—Eduardo C. Robert
(74) Attorney, Agent, or Firm—Vidas, Arrett & Steinkraus, P.A.

(57) ABSTRACT

A stent delivery system which includes a catheter having a radially expandable stent coaxially arranged near a distal end of the catheter. The catheter is equipped with at least one stent securement hub disposed about a portion of the distal end of the catheter underlying the stent. Each of the at least one stent securement hubs being made of a radiopaque polymer.

10 Claims, 1 Drawing Sheet

RADIOPAQUE MARKER BANDS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, such as greater than about four atmospheres, to radially compress the artirosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be injury to or restenosis of the artery, which either necessitates another angioplasty procedure, a surgical by-pass operation, or some method of repairing or strengthening the area. To strengthen the area and help prevent restenosis, a physician can implant an intravascular prosthesis for maintaining vascular patency, commonly called a stent, inside the artery at the lesion. The stent is expanded to a larger diameter for placement in the vasculature, often by the balloon portion of the catheter. Stents delivered to a restricted coronary artery, expanded to a larger diameter by a balloon catheter, and left in place in the artery at the site of a dilated lesion are shown in U.S. Pat. No. 4,740,207 to Kreamer and U.S. Pat. No. 5,007,926 to Derbyshire, the content of which is incorporated herein by reference. Palmaz et al., 156 *Radiology* 73 (1985) and U.S. Pat. No. 4,733,665 describe introduction of a stent over a balloon catheter (incorporated herein by reference).

To assist in accurate placement of the catheter and stent underneath the lesion site it is useful to visually monitor the catheter as it advances through a vessel. Fluoroscopes or other similar X-ray emitting devices are used to view the catheter within the body as it is advanced. However, in order for the catheter to be visible when exposed to X-rays, the catheter or a portion of the catheter, must be radiopaque to X-rays. In previous catheter designs, radiopaque marker bands or catheter tips are often attached to the catheter for this purpose.

An initial example of a catheter which utilizes an external metal radiopaque marker band is U.S. Pat. No. 5,759,174 to Fischell et al., the entire contents of which are hereby incorporated by reference, which has a single external metal marker band which is intended to identify the central portion of a stenosis once the delivery catheter is removed. Marker bands such as those disclosed by Fischell et al. are normally mounted externally on the delivery catheter and undesirably increase the profile of the catheter as well as its cost. Furthermore, marker bands are constructed from expensive and heavy radiopaque metals such as gold, platinum and tantalum or alloys of these dense materials. Marker bands constructed from these metals are also costly to manufacture.

Despite these shortcomings, marker bands are preferable over radiopaque tips alone, since a radiopaque catheter tip only provides for the end of the catheter to be visible as opposed to a desired area along the catheter shaft. For example, U.S. Pat. No. 5,429,597 to Demello et al., the entire contents of which are hereby incorporated by reference, discloses a balloon catheter having a radiopaque distal tip composed of a polymer mixed with a radiopaque powder such as tungsten. Such a tip is visible under X-ray observation. In addition Demello et al., discloses a preferred embodiment which uses of two metal radiopaque marker bands located along a core wire to better track the expandable region of a balloon.

U.S. Pat. No. 4,866,132 to Obligin et al.; U.S. Pat. No. 5,256,334 to Smid et al.; and U.S. Pat. No. 5,024,232 to Smid et al., the entire contents of each being hereby incorporated by reference, respectively disclose various methods of making radiopaque polymer complexes. The references also suggest using radiopaque polymer complexes with existing implantable devices which are presently used with radiolucent plastics. These references do not however, disclose the present catheter which is constructed with radiopaque polymer hubs as disclosed below, and where the hubs provide the dual function of stent crimping and marker bands.

BRIEF SUMMARY OF THE INVENTION

The present invention provides for a stent delivery system. The stent delivery system comprises, a balloon catheter having a proximal end and a distal end, the catheter having at least one radially mounted stent securement hub located near the distal end, the stent securement hub being made of a radiopaque polymer. The catheter includes a stent receiving portion adapted to receive a stent over the balloon and the radiopaque stent securement hub.

In the preferred embodiment of the invention the basic components of the stent delivery system consist of a catheter having a noncompressible inner shaft, an outer shaft, and two radiopaque stent mounting hubs coaxially arranged about the inner shaft. The two radiopaque hubs have a diameter greater than that of the inner shaft and rest underneath the stent and balloon, defining the stent mounting region. The hubs are spaced to match the length of the stent, thereby providing a visual guide for accurate placement and deployment when viewed with a fluoroscope or other x-ray emitting device. Alternatively, the portion of the inner shaft upon which the stent is mounted may be radiopaque.

The radiopaque quality of the hubs or shaft is provided for by constructing the hubs with a typical polymer material and adding a radiopaque substance from the group consisting of barium, bismuth, tungsten, gold, titanium, iridium, platinum or rhenium. In a preferred embodiment high density polyethylene is mixed with a predetermined amount of tungsten, such as 80% tungsten by weight.

Thus, an object of the present invention is to provide for a low profile stent delivery catheter which incorporates a relatively low cost radiopaque polymer material to define the stent mounting region, so that the stent mounting region may be visible when exposed to X-rays and be more accurately positioned within a bodily vessel as a result.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
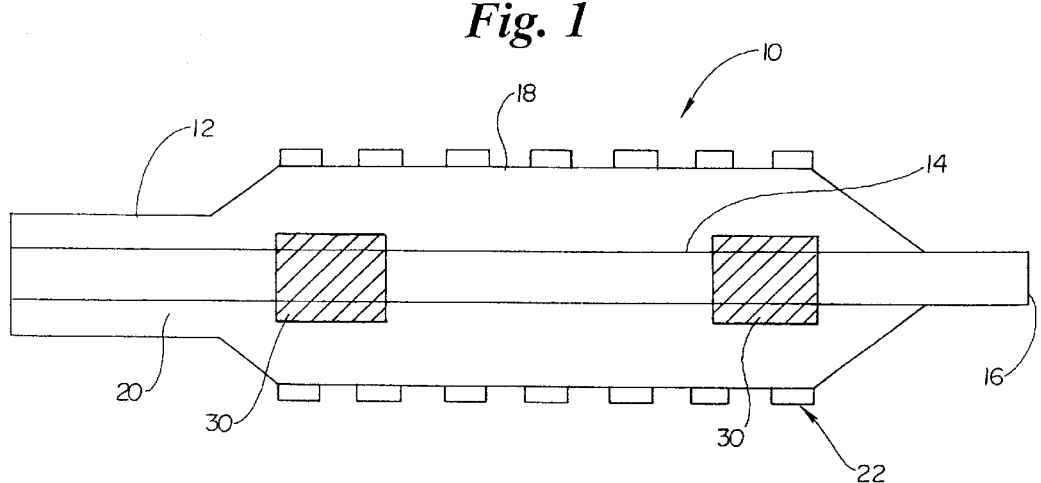
FIG. 1 is a longitudinal cross-sectional view of the present stent delivery catheter showing the balloon in a partially inflated state with a balloon expandable stent.

FIG. 1 shows a longitudinal cross-section of a specific preferred embodiment of a stent delivery system that is the subject of the present invention. The device generally comprises a catheter, shown generally at 10, comprising a proximal outer shaft 12 of a predetermined length and an inner shaft 14, the outer shaft forming an outer body portion which covers the majority of the inner shaft excluding a portion of the distal end of the inner shaft. The inner shaft 14 may be configured to as a guide wire lumen as is well known in the art.

The proximal outer shaft 12 encloses inner shaft 14 which is longer than outer shaft 12 and extends through and beyond outer shaft 12 to terminate at the distal tip 16 of the catheter 10. Preferably the inner shaft 14 encloses a guide wire (not shown) which aids in the navigation of the catheter through the appropriate vessel. The inner shaft 14 is preferably made of flexible, but incompressible construction such as a polymer encapsulated braid or coil as is known within the art. It should be noted that the present stent delivery catheter could utilize a guide wire in any of the well known fixed-wire, over-the-wire, or rapid exchange configurations.

A balloon or inflation means 18 is attached at its distal end to the inner shaft 14 just proximal to the distal tip 16. The proximal end of the balloon 18 is attached to the outer shaft 12. The resulting space between the inner shaft 14 and the outer shaft 12 defines an inflation lumen 20 which is operatively connected to the proximal end of the stent delivery catheter. The inflation lumen 20, is controlled by an operator at the proximal end of the stent delivery catheter as is well known in the art.

A medical device such as stent 22 is carried on inner shaft 14 above balloon 18, as is well known in the art. Stent 22 can be self-expanding or balloon expandable. The inventive catheter may be used to delivery endovascular stent grafts, vena cava filters, aneurysm repair particles, self-expanding stents, balloon expandable stents, or the like.

The stent is initially secured around the balloon 18 in a crimped or unexpanded form. As the balloon 18 is inflated by fluid passing through the inflation lumen 20 the stent 22 will be expanded with the balloon.

Figure 2:
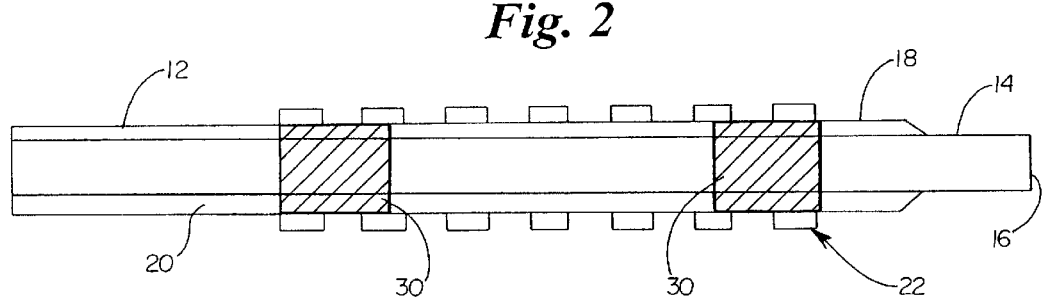
FIG. 2 shows the catheter of FIG. 1 with the stent in its crimped form.

In both FIGS. 1 and 2 two stent mounting hubs 30 are shown disposed about the inner shaft 14. The hubs 30 are constructed to provide a surface to which the stent can be held against when the stent is in its crimped form, as best shown in FIG. 2. Such hub configurations are well known in the art. The hubs may be moveable along the inner shaft 14 by incorporating any of the well known securing devices such as fasteners, tabs, etc. In the embodiment shown in the various figures the hubs 30 are positioned on the inner shaft 14 to correspond with the edges of the stent 22. Such a configuration allows the stent to be held at both ends thereby preventing one of the stent ends from flaring and possibly damaging the vessel wall.

The stent mounting hubs 30 are radiopaque and are thus visible within the body when viewed with a fluoroscope or other X-ray emitting device. However, the hubs 30 are not composed of a heavy metal or alloy alone as marker bands typically are, but instead are a mixture of a radiopaque substance and a polymer. While such radiopaque substances could include the commonly utilized metals such as barium, bismuth, tungsten, gold, titanium, platinum, iridium, or rhenium; the amount of metal is reduced since it is mixed with a significant amount of polymer such as a high density polyurethane.

As a result of the unique composition of the hubs 30 and their placement along the inner shaft 14 to correspond with the edges of the stent 22, the hubs will function as both radiopaque markers for more precise placement of the stent within a bodily vessel, as well as to provide a means for securing a crimped stent to the inner shaft 14.

Figure 3:
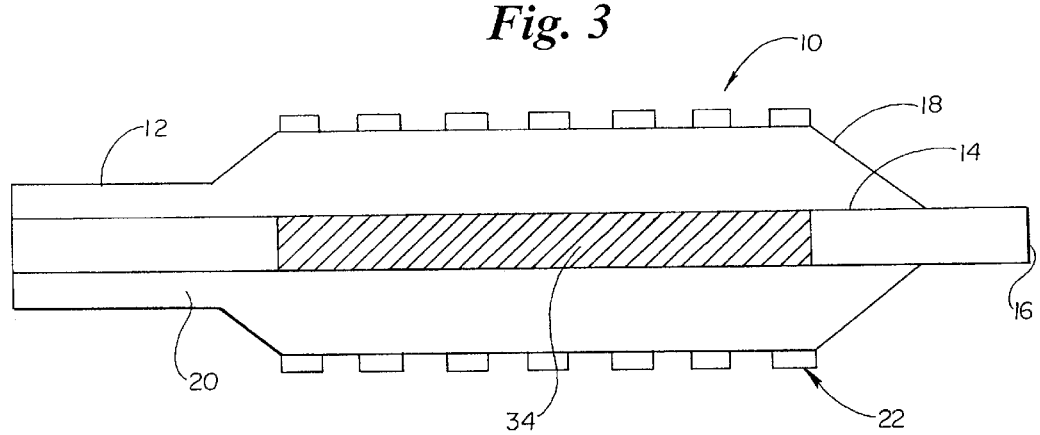
FIG. 3 shows a further embodiment of the stent shown in FIG. 1 wherein the hubs are replaced with a radiopaque region on the inner shaft directly.

In FIG. 3, an alternative embodiment is shown wherein the entire inner shaft 14 or more preferably the portion of the inner shaft which underlies the stent 22 or balloon 18 is composed of a radiopaque polymer as described above. Such a radiopaque region 34 will allow the catheter to have an even lower profile by avoiding the use of any mounting hubs. Furthermore, such an embodiment will allow for even more precise visual tracking of the stent mounting region under X-rays.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent delivery system comprising:
   a catheter having a proximal end and a distal end, the catheter having at least one stent securement hub located near the distal end, the stent securement hub being made of a radiopaque polymer;
   a radially expandable stent coaxially arranged near the end of the catheter, the stent having a crimped state and an uncrimped state, the at least one stent securement hub being located underneath the radially expandable stent;
   an inflation balloon located underneath the stent and above the at least one stent securement hub, the at least one stent securement hub providing a surface about which the stent is secured when the stent is in the crimped state.

2. The stent delivery system of claim 1, wherein the catheter further comprises a shaft, at least a portion of the shaft being constructed from a radiopaque polymer.

3. The stent delivery system of claim 2, wherein the at least a portion of the shaft constructed from a radiopaque polymer defines a stent mounting region.

4. The stent delivery system of claim 2, wherein the at least one stent securement hub is coaxially arranged around the shaft.

5. The stent delivery system of claim 4, wherein the at least one stent securement hub has a greater diameter than that of the shaft.

6. The stent delivery system of claim 2, wherein the radiopaque polymer includes a radiopaque substance from the group consisting of barium, bismuth, tungsten, gold, titanium, iridium, platinum or rhenium and a polymer.

7. The stent delivery system of claim 6 wherein the at least a portion of the shaft is constructed from a predetermined amount of tungsten, by weight, in combination with high density polyethylene.

8. The stent delivery system of claim 7, wherein the amount of tungsten, by weight, is 80%.

9. The stent delivery system of claim 1, wherein the at least one stent securement hub is comprised of a first stent securement hub and a second stent securement hub, the first sent securement hub positioned on the shaft to receive a first end of the stent and the second stent securement hub being positioned on the shaft to correspond with a second end of the stent.

10. The stent delivery system of claim 1, wherein the radiopaque polymer includes a radiopaque substance from the group consisting of barium, bismuth, tungsten, gold, titanium, iridium, platinum or rhenium.

\* \* \* \* \*